United States Patent [19]

Saito et al.

[11] Patent Number: 5,629,420

[45] Date of Patent: May 13, 1997

[54] SUBSTITUTED ACETOXYAZETIDINONE DERIVATIVES AND PROCESS FOR PREPARING 4-ACYLOXYAZETIDINONE DERIVATIVES

[75] Inventors: Takao Saito; Hidenori Kumobayashi, both of Tokyo; Shunichi Murahashi, Osaka, all of Japan

[73] Assignee: Takasago International Corporation, Tokyo, Japan

[21] Appl. No.: 436,810

[22] Filed: May 8, 1995

Related U.S. Application Data

[62] Division of Ser. No. 167,201, Dec. 16, 1993, Pat. No. 5,440,030, which is a division of Ser. No. 869,171, Apr. 16, 1992, Pat. No. 5,288,862.

[30] Foreign Application Priority Data

Apr. 18, 1991 [JP] Japan .................................. 3-86588

[51] Int. Cl.$^6$ ...................... C07B 41/12; C07D 205/08
[52] U.S. Cl. ...................................................... 540/357
[58] Field of Search ........................................... 540/357

[56] References Cited

U.S. PATENT DOCUMENTS

| | | | |
|---|---|---|---|
| 4,845,210 | 7/1989 | Nakai et al. | 540/200 |
| 4,923,982 | 5/1990 | Lynch et al. | 540/200 |
| 4,940,520 | 7/1990 | Lynch et al. | 540/200 |
| 5,081,239 | 1/1992 | Saito et al. | 540/200 |
| 5,204,460 | 4/1993 | Saito | 540/357 |

FOREIGN PATENT DOCUMENTS 0247378  12/1987  European Pat. Off. .

OTHER PUBLICATIONS

*Heterocycles*, vol. 17, pp. 463–506 (1982).
*Tetrahedron Letters*, vol. 23, No. 22, pp. 2293–2296 (1982).
*Tetrahedron Letters*, vol. 29, No. 12, pp. 1409–1412 (1988).
*Tetrahedron*, vol. 41, pp. 4367–4416 (1985).
*Tetrahedron Letters*, vol. 32, No. 19, pp. 2145–2148 (1991).
*Tetrahedron Letters*, vol. 32, No. 42, pp. 5991–5994 (1991).

*Primary Examiner*—Mark L. Berch

*Attorney, Agent, or Firm*—Sughrue, Mion, Zinn, Macpeak & Seas

[57] ABSTRACT

A process for preparing a 4-acyloxyazetidinone or a derivative thereof represented by formula (IV):

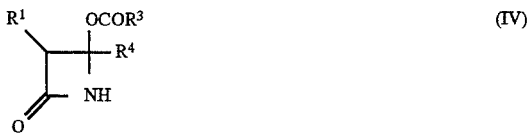

wherein $R^1$ represents a hydrogen atom, a lower alkyl group, a hydroxyethyl group, or a protected hydroxyethyl group; $R^3$ represents an alkyl group having from 1 to 10 carbon atoms which may be substituted with a halogen atom, a cyano group, a lower alkoxy group or a phenyl group, or a substituted or unsubstituted phenyl group, provided that the α-positioned carbon atom of said alkyl group should not have more than two halogen atoms; and $R^4$ represents a hydrogen atom, a lower alkyl group, or a lower alkoxycarbonyl group, which is useful as an intermediate for penem antibiotics is disclosed, comprising reacting azetidinone or a derivative thereof represented by formula (II):

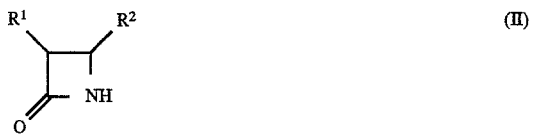

wherein $R^1$ is as defined above, and $R^2$ represents a hydrogen atom, a lower alkyl group, a lower alkoxycarbonyl group, or a carboxyl group, with a carboxylic acid represented by formula (III):

$R^3COOH$  (III)

wherein $R^3$ is as defined above, in the presence of (1) a transition metal compound selected from a ruthenium compound, an osmium compound, and a cobalt compound, (2) an aldehyde having 2 or more carbon atoms, provided that the carbon atom at the α-position thereof should not have two or more halogen atoms, and (3) oxygen. The compound (IV) can be prepared with safety through simple and easy operations.

4 Claims, No Drawings

SUBSTITUTED ACETOXYAZETIDINONE DERIVATIVES AND PROCESS FOR PREPARING 4-ACYLOXYAZETIDINONE DERIVATIVES

This is a divisional of application Ser. No. 08/167,201, filed Dec. 16, 1993, now U.S. Pat. No. 5,440,030 which is a divisional of prior application Ser. No. 07/869,171, filed Apr. 16, 1992 (now U.S. Pat. No. 5,288,862).

FIELD OF THE INVENTION

This invention relates to a process for preparing a useful intermediate for synthesizing penem antibiotics exemplified by thienamycin. More particularly, it relates to a process for preparing a 4-acyloxyazetidinone represented by formula (IV):

wherein $R^1$ represents a hydrogen atom, a lower alkyl group, a hydroxyethyl group, or a protected hydroxyethyl group; $R^3$ represents an alkyl group having from 1 to 10 carbon atoms which may be substituted with a halogen atom, a cyano group, a lower alkoxy group or a phenyl group, or a substituted or unsubstituted phenyl group, provided that the α-positioned carbon atom of said alkyl group should not have more than two halogen atoms; and $R^4$ represents a hydrogen atom, a lower alkyl group, or a lower alkoxycarbonyl group.

BACKGROUND OF THE INVENTION

Penem antibiotics represented by thienamycin have attracted attention as medicines because of their broad antimicrobial spectra.

Various processes for preparing penem antibiotics have been reported, e.g., in Kametani, *Heterocycles*, Vol. 17, pp. 463–506 (1982) and Shibuya, et al., *Yuki Gosei Kagaku*, Vol. 41, p. 62 (1983). Among the known processes, a process using a 4-acyloxyazetidinone or a derivative thereof represented by formula (IV) as an intermediate is particularly advantageous in that the compound of formula (IV) is reactive with various nucleophilic agents, leading to various penem antibiotics.

Known processes for preparing the intermediate compound of formula (IV) include oxidation of 4-carboxyazetidinone derivatives with lead tetraacetate (*Tetrahedron Letters*, Vol. 23, p. 2293 (1982)), electrode oxidation of 4-carboxyazetidinone derivatives (*Tetrahydron Letters*, Vol. 29, p. 1409 (1988)), oxidation of 4-acetylazetidinone derivatives with m-chloroperbenzoic acid (JP-A-61-50964) (the term "JP-A" as used herein means an "unexamined published Japanese patent application"), and treatment of 4-silyloxyazetidinone derivatives with acetic anhydride (European Patent 247,378).

In order to introduce an acetoxy group to the 4-position of the azetidinone skeleton according to any of the above-described processes, it is necessary to synthesize an azetidinone compound having a specific substituent group at the 4-position, via which an acetoxy group is to be introduced. However, preparation of an azetidinone compound having such a specific substituent group at the 4-position involves complicated steps and, also, it has been difficult to convert the substituent group at the 4-position to an acetoxy group. Hence, these conventional processes are not regarded advantageously as industrial techniques.

Other processes for synthesizing 4-acyloxyazetidinone derivatives are described in JP-A-3-48681 and JP-A-3-56481, but they have industrial disadvantages such as low yields, in addition to the above-described problems.

On the other hand, it has lately been suggested to react an azetidinone compound with acetic acid and a peroxide as an oxidizing agent in the presence of a ruthenium compound catalyst to introduce an acetoxy group as disclosed in JP-A-2-231471. However, many of the peroxides useful as an oxidizing agent are generally dangerous, demanding meticulous care not only in storage and transportation but on actual use. Besides the safety problem, they are expensive.

Further, 4-acetoxyazetidinone derivatives are still unsatisfactory due to the insufficient activity of the 4-positioned acetoxy group as a releasable group, and it is desired to develop an intermediate having a more active releasable group. It is known that the activity of a releasable group increases and becomes more advantageous in the displacement reaction at the 4-position as its acidity increases (see W. N. Speckamp and H. Hiemstra, *Tetrahedron*, Vol. 41, p. 4367 (1985)). From this point of view, it is anticipated that a chloroacetoxy group, a cyanoacetoxy group, a bromoacetoxy group, a dichloroacetoxy group, a dibromoacetoxy group, and the like are more active than an acetoxy group.

In particular, while carbon nucleophilic agents used in reactions for forming a carbon-to-carbon bond by using a Lewis acid, etc., such as ketene silyl acetal and silyl enol ether, are relatively labile under the reaction conditions, such lability would be compensated for by increasing the reaction rate by using an intermediate with the above-mentioned active releasable group. Nevertheless, it has been difficult to synthesize such an intermediate from 4-acetoxy compounds through conventional techniques such as ester exchange reaction.

SUMMARY OF THE INVENTION

An object of the present invention is to provide a process for preparing a 4-acyloxyazetidinone compound by introducing an acyloxy group to the 4-position of an azetidinone compound with safety and in good yield through simple and easy operations.

In the light of the above situation, the inventors have conducted extensive investigations. As a result, it has now been found that the above object of the present invention is accomplished by reacting an azetidinone compound and a carboxylic acid in the presence of (1) a transition metal compound selected from a ruthenium compound, an osmium compound, and a cobalt compound, (2) an aldehyde, and (3) oxygen. The present invention has been completed based on this finding.

The present invention provides a process for preparing a 4-acyloxyazetidinone or a derivative thereof represented by formula (IV), which comprises reacting azetidinone or a derivative thereof represented by formula (II):

wherein $R^1$ is as defined above, and $R^2$ represents a hydrogen atom, a lower alkyl group, a lower alkoxycarbonyl group, or a carboxyl group, with a carboxylic acid represented by formula (III):

R³COOH    (III)

wherein R³ is as defined above, in the presence of (1) a transition metal compound selected from a ruthenium compound, an osmium compound, and a cobalt compound, (2) an aldehyde having 2 or more carbon atoms in which the carbon atom at the α-position should not have two or more halogen atoms, and (3) oxygen.

DETAILED DESCRIPTION OF THE INVENTION

In the present invention, the term "lower" in the "lower alkyl group" or "lower alkoxy group" usually means 1 to 5 carbon atoms, and the term "lower" in the "lower alkanoyloxy group" usually means 2 to 6 carbon atoms.

Examples of the starting azetidinone compound of formula (II) which can be used in the present invention are azetidin-2-one, 3-methylazetidin-2-one, 3-ethylazetidin-2-one, 3-(protected) hydroxyethylazetidin-2-one, 3-methyl-4-carboxyazetidin-2-one, 3-ethyl-4-carboxyazetidin-2-one, 3-(protected) hydroxyethyl-4-carboxyazetidin-2-one, 4-methylazetidin-2-one, 4-carboxyazetidin-2-one, and 4-methoxycarbonylazetidin-2-one. The protective groups for a hydroxyl group include those commonly employed for hydroxyl group protection in lactam compounds, e.g., silyl groups (e.g., trimethylsilyl, triethylsilyl, t-butyldimethylsilyl, diphenyl-t-butylsilyl), a benzyloxycarbonyl group, a p-nitrobenzyloxycarbonyl group, and an o-nitrobenzyloxycarbonyl group.

Of the compounds of formula (II), those wherein R¹ is a protected or unprotected hydroxyethyl group, and R³ is a hydrogen atom can be prepared, for example, in accordance with the processes described in *Ber.*, Vol. 92, p. 1599 (1959) and JP-A-2-231471.

Of the carboxylic acids of formula (III), those wherein R³ is an alkyl group having from 1 to 10 carbon atoms include acetic acid, propionic acid, butyric acid, hexanoic acid, heptanoic acid, octanoic acid, decanoic acid, and isobutyric acid. The number of substituent groups on the alkyl group R³ is not particularly limited except that the number of halogen atoms on the α-positioned carbon atom, if any, is limited to 1 or 2. If a carboxylic acid having three halogen atoms at the α-position thereof, e.g., trichloroacetic acid, is used, some influence is exerted onto the substrate, failing to obtain a desired compound.

Examples of carboxylic acids (III) wherein R³ is a halogen-substituted alkyl group include chloroacetic acid, dichloroacetic acid, bromoacetic acid, dibromoacetic acid, 3-chloropropionic acid, 2-bromohexanoic acid, and 2-bromooctanoic acid. Examples of carboxylic acids (III) wherein R³ is a lower alkoxy-substituted alkyl group include methoxyacetic acid and 3-ethoxypropionic acid. Examples of carboxylic acids (III) wherein R³ is a cyano-substituted alkyl group include cyanoacetic acid. Examples of carboxylic acids (III) wherein R³ is a phenyl-substituted alkyl group include phenylacetic acid, 2-phenylbutyric acid, and 6-phenylhexanoic acid. Examples of carboxylic acids (III) wherein R³ is a substituted or unsubstituted phenyl group include benzoic acid, p-chlorobenzoic acid, p-ethoxybenzoic acid, and 2,4-dinitrobenzoic acid.

The transition metal compound used in the present invention serves as a catalyst.

Ruthenium compounds include the following compounds (a) to (j).

(a) Compounds represented by formula (V):

$$RuA_3 \quad (V)$$

wherein A represents a halogen atom, a lower alkanoyloxy group, or acetylacetonato.

Specific examples of the compounds (V) are ruthenium trichloride, ruthenium tribromide, ruthenium triiodide, and hydrates of these ruthenium halides; rutheniumacetylacetonate; and ruthenium acetate.

(b) Metallic ruthenium or ruthenium-on-carrier:

Metallic ruthenium includes ruthenium powder. Examples of the ruthenium-on-carrier include ruthenium-on-carbon, ruthenium-on-graphite, ruthenium-on-alumina, ruthenium-on-silica, ruthenium-on-silica-alumina, ruthenium-on-zeolite, ruthenium-on-iron oxide, ruthenium-on-zirconium oxide, and ruthenium-on-diatomaceous earth.

(c) Compounds represented by formula (VI):

$$[Ru_rCl_mH_n(N_2)_jB_p]_q \quad (VI)$$

wherein B represents $PR^5{}_3$, wherein $R^5$ represents a phenyl group which may be substituted with a lower alkyl group or a lower alkoxy group, or a lower alkyl group; when $R^5$ is a phenyl group which may be substituted with a lower alkyl group or a lower alkoxy group, (i) m=0, n=2, j=0, p=4, q=1, and r=1, (ii) m=0, n=2, j=1, p=3, q=1, and r=1, (iii) m=1, n=1, j=0, p=3, q=1, and r=1, or (iv) m=2, n=0, j=0, p=3, q=1, and r=1; and when $R^5$ is a lower alkyl group, (i') m=3, n=0, j=0, p=2, q=2, and r=1 or (ii') m=5, n=0, j=0, p=3, q=1, and r=2.

Specific examples of the compounds (VI) are RuHCl(PPh₃)₃, RuCl₂(PPh₃)₃, RuH₂(PPh₃)₃, RuH₂(N₂)(PPh₃)₃, [RuCl₃(PBu₃)₂]₂, and Ru₂Cl₅(PBu₃)₃, wherein Ph represents a phenyl group, and Bu represents a butyl group.

(d) Compounds represented by formula (VII):

$$[RuY_2L]_m \quad (VII)$$

wherein Y represents a chlorine atom, a bromine atom, or an iodine atom; m represents a positive integer; and L represents 1,5-cyclooctadiene, norbornadiene, cyclooctatetraene, cycloheptatriene, benzene, or lower alkyl-substituted benzene.

Specific examples of the compounds (VII) are RuCl₂(COD), RuCl₂(NBD), RuCl₂(COT), RuBr₂(COD), RuBr₂(NBD), RuBr₂(COT), RuI₂(COD), RuI₂(NBD), RuI₂(COT), RuCl₂(CHPT), RuBr₂(CHPT), RuCl₂(C₆H₆), RuBr₂(C₆H₆), RuI₂(C₆H₆), RuCl₂(C₆H₅CH₃), RuCl₂-[p-C₆H₄(CH₃)₂], RuCl₂[1,3,5-C₆H₃(CH₃)₃], and RuCl₂[p-cymene], wherein COD represents 1,5-cyclooctadiene; NBD represents norbornadiene; COT represents cyclooctatetraene; and CHPT represents cycloheptatriene.

(e) Compounds represented by formula (VIII):

$$Ru_xH_yCl_z(R\text{-BINAP})_2(S)_p \quad (VIII)$$

wherein R-BINAP represents tertiary phosphine represented by formula (IX):

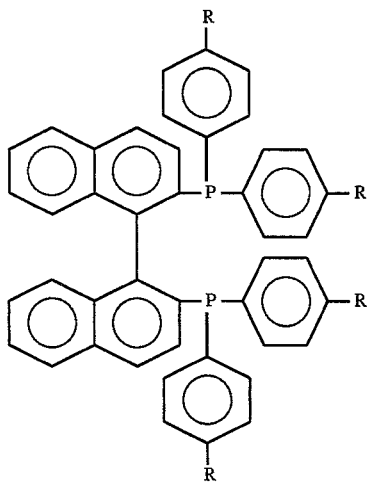

wherein R represents a hydrogen atom, a methyl group, or a t-butyl group; (S) represents a tertiary amine; y represents 0 or 1; when y is 0, x=2, z=4, and p=1; and when y is 1, x=1, z=1, and p=0, (f) Compounds represented by formula (X):

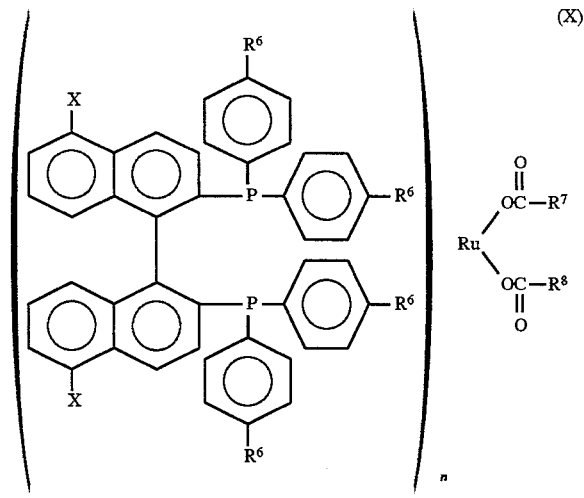

wherein X represents a hydrogen atom, an amino group, an acetylamino group, or a sulfone group; $R^6$ represents a hydrogen atom or a lower alkyl group; $R^7$ and $R^8$ each represent a lower alkyl group, a halogenated lower alkyl group, a phenyl group, a lower alkyl-substituted phenyl group, an α-aminoalkyl group, or an α-aminophenylalkyl group, or they are taken together to form an alkylene group; and n represents 1 or 2, (g) Compounds represented by formula (XI):

[RuH$_l$(R-BINAP)$_m$]Z$_n$  (XI)

wherein R-BINAP is as defined above; Z represents ClO$_4$, BF$_4$, or PF$_6$; l represents 0 or 1; when l is 0, m=1 and n=2; and when l is 1, m=2 and n=1, (h) Compounds represented by formula (XII):

[RuT$_l$M$_m$(R-BINAP)]K$_n$  (XII)

wherein R-BINAP is as defined above; T represents a halogen atom; M represents substituted or unsubstituted benzene or acetonitrile; K represents a halogen atom, ClO$_4$, PF$_6$, BPh$_4$ (wherein Ph represents a phenyl group), or BF$_4$; when M is substituted or unsubstituted benzene, l=1, m=1, and n=1; and when M is acetonitrile, when l is 1, m=2 and n=1, and when l is 0, m=4 and n=2, (i) Ru$_3$(CO)$_{12}$, RuI$_2$(CO)$_2$, Ru$_2$Cl$_4$(CO)$_6$, Ru(CO)$_5$, and Ru(TPP)(CO)—THF, wherein TPP represents tetrahydrofuran.

(j) Ru(NO)Cl$_3$.H$_2$O, Ru(NO)Br$_3$.H$_2$O, K(RuO$_4$), and Ba(RuO$_3$(OH)$_2$).

The osmium compounds include compounds represented by formula (XIII):

OsY$_3$  (XIII)

wherein Y represents a chlorine atom, a bromine atom, or an iodine atom.

Specific examples of the compounds (XIII) are osmium trichloride, osmium tribromide, osmium triiodide, and hydrates of these osmium halides.

The cobalt compounds include compounds represented by formula (XIV):

CoW$_2$  (XIV)

wherein W represents a chlorine atom, a bromine atom, an iodine atom, or an acetoxy group.

Specific examples of the compounds (XIV) are cobalt chloride, cobalt bromide, cobalt iodide, cobalt acetate, and hydrates thereof.

The compounds (VI) can be obtained by the processes described in The Chemical Society of Japan (ed.), *SHIN-JIKKEN KAGAKU KOZA*, Vol. 12 (YUKI KINZOKU KAGAKU), p. 163, Maruzen (Mar. 20, 1976) and *J. C. S., Dalton Trans*, p. 2480 (1980). The compounds (VII) can be synthesized by the processes disclosed in *Chemistry and Ind.*, p. 1516 (1959), *J. C. S.*, p. 3178 (1959), *J. Organometal.*, Vol. 7, p. 487 (1967), and *J. C. S., Dalton Trans*, p. 233 (1974). The compound (VII) as produced comprises, in some cases, solely of the compound wherein m is 1 and, in some other cases, a mixture of the compound wherein m is 1 and polymers thereof (i.e., m is 2 or more). For the sake of convenience, the latter compound will hereinafter be expressed as a compound wherein m is 1. The compounds (VIII), (X), (XI), and (XII) can be prepared by the processes disclosed in JP-A-61-63690, JP-A-62-265293, JP-A-63-41487, and JP-A-2-191289, respectively.

The aldehydes having 2 or more carbon atoms which can be used in the present invention are not particularity restricted and include alkylaldehydes, alkenylaldehydes, and arylaldehydes, each of which may be substituted provided the α-positioned carbon atom thereof should not have more than 2 halogen atoms. Examples of the substituted or unsubstituted alkylaldehydes are acetaldehyde, propionaldehyde, butyraldehyde, hexanal, heptanal, octanal, decanal, dodecanal, isopropionaldehyde, isobutyraldehyde, chloroacetaldehyde, dichloroacetaldehyde, fluoroacetaldehyde, bromoacetaldehyde, α-chloropropionaldehyde, α-bromopropionaldehyde, 1-chlorooctanal, phenylacetaldehyde, p-methoxyphenylacetaldehyde, p-chlorophenylacetaldehyde, m-chlorophenylacetaldehyde, cyclohexanecarbaldehyde, and cyclopentanecarbaldehyde. Examples of the substituted or unsubstituted alkenylaldehydes are crotonaldehyde, 2-pentenal, and 2-hexenal. Examples of the substituted or unsubstituted arylaldehydes are benzaldehyde, p-chlorobenzaldehyde, m-chlorobenzaldehyde, p-methoxybenzaldehyde, o-methoxybenzaldehyde, 3,4-dimethoxybenzaldehyde, p-methylbenzaldehyde, piperonal, 1-formylnaphthalene, and 2-formylnaphthalene.

For obtaining improved yields, it is preferable to use an aldehyde corresponding to the carboxylic acid used.

Oxygen to be used in the reaction may be oxygen gas or an oxygen-containing gas, e.g., air.

The reaction is preferably carried out in the co-presence of a carboxylic acid salt to increase the yield. Any carboxylic acid salts, e.g., sodium acetate, potassium acetate and lithium acetate, may be used, but a salt of the same carboxylic acid used in the reaction is preferred.

In carrying out the present invention, the compound (II), aldehyde, carboxylic acid (III), and transition metal compound are dissolved or suspended in an appropriate solvent, and the solution or suspension is stirred at a temperature of from −10° to 80° C., and preferably from 0° to 40° C., for a period of from 0.5 to 15 hours, and preferably from 1 to 5 hours, while introducing oxygen or an oxygen-containing gas into the reaction system. While the order or mode of addition of the starting compounds, catalyst, etc. are not particularly limited, it is recommended to add the aldehyde finally.

Examples of useful solvents include methyl acetate, ethyl acetate, butyl acetate, acetone, methyl ethyl ketone, methyl butyl ketone, dichloromethane, acetonitrile, and chloroform. Mixtures of these solvents are also useful. The aldehyde is used in an amount usually of from 1 to 5 mole, and preferably from 1.1 to 3 mole, per mole of the compound (II). The carboxylic acid (III) is used in an amount usually of from 1 to 15 mole, and preferably from 2 to 10 mole, per mole of the compound (II). The transition metal compound is used in an amount usually of from 0.001 to 0.1 mole, and preferably from 0.01 to 0.05 mole, per mole of the compound (II).

Methods of isolation and purification of the product from the reaction mixture are not restricted. For example, re-crystallization and column chromatography may be performed.

Of the 4-acyloxyazetidinone or derivatives thereof of formula (IV) obtained by the present invention, a substituted acetoxyazetidinone derivative represented by formula (I):

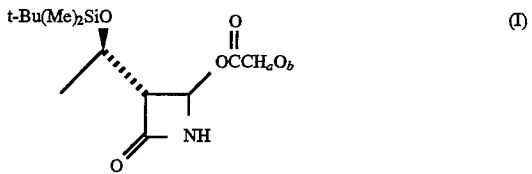

wherein t-Bu represents a t-butyl group; Me represents a methyl group; D represents a chlorine atom, a bromine atom, or a cyano group; a represents 1 or 2; and b represents 2 when a is 1, or b represents 1 when a is 2, is a novel compound.

The novel compounds of formula (I) exhibit higher activity at the 4-positioned releasable group as compared with 4-acetoxyazetidinone compounds and are therefore superior as intermediates for synthesizing carbapenem antibiotics.

The above-described process of the present invention holds industrial advantages in that a 4-acyloxyazetidinone or a derivative thereof (IV) useful as intermediates for penem antibiotics can be prepared with safety through simple and easy operations.

The present invention is now illustrated in greater detail with reference to Examples, but it should be understood that the present invention is not construed as being limited thereto. All the parts, percents, and ratios are by weight unless otherwise indicated.

EXAMPLE 1

Synthesis of 4-Acetoxyazetidin-2-one

In a Schlenk's tube were charged 710 mg (10 mmole) of azetidin-2-one, 205 mg (2.5 mmole) of anhydrous sodium acetate, and 130 mg (0.5 mmole, 5 mole %) of ruthenium chloride trihydrate. After thoroughly displacing the atmosphere with oxygen, a balloon filled with oxygen was fitted to the reactor. To the mixture were added 100 ml of ethyl acetate and 5 ml of acetic acid, followed by heating at 40° C. for 30 minutes with stirring. To the reaction mixture was added 1.1 ml (20 mmole) of acetaldehyde all at once while stirring at 40° C., and the reaction was continued for an additional 3 hours. The reaction mixture was poured into 400 ml of a 10% sodium sulfite aqueous solution and extracted twice with 500 ml portions of ethyl acetate. The extract was washed with 200 ml of a saturated sodium chloride aqueous solution and dried over anhydrous sodium sulfate. The solvent was removed by distillation under reduced pressure, and the residue was purified by silica gel column chromatography using a 3:1 (by volume) mixed solvent of n-hexane and ethyl acetate to obtain 1.14 g (8.8 mmole, percent yield: 88%) of 4-acetoxyazetidin-2-one as an oily substance.

EXAMPLES 2 TO 5

4-Acetoxyazetidinone or a derivative thereof shown in Table 1 below was prepared in the same manner as in Example 1, except for replacing the substrate, azetidin-2-one, with each of the azetidinone compounds of Table 1. In the formulae in Table 1, t-Bu represents a t-butyl group; Me represents a methyl group; and Ac represents an acetyl group.

TABLE 1

| Example No. | Substrate | Produced 4-Acetoxy-azetidinone Compound | Yield (%) |
|---|---|---|---|
| 2 | t-Bu(Me)₂SiO [structure with NH] | t-Bu(Me)₂SiO [structure with OAc, NH] | 91 |
| 3 | CH₃ [structure with NH] | CH₃ [structure with OAc, NH] | 72 |

TABLE 1-continued

| Example No. | Substrate | Produced 4-Acetoxy-azetidinone Compound | Yield (%) |
|---|---|---|---|
| 4 | (structure with COOH, NH) | (structure with OAc, NH) | 87 |
| 5 | (structure with CO₂Me, NH) | (structure with CO₂Me, OAc, NH) | 72 |

EXAMPLES 6 TO 14

Synthesis of (1'R,3R,4R)-4-Acetoxy-3-[(1'-t-butyldimethylsilyloxy)ethyl]azetidin-2-one The titled compound was synthesized in the same manner as in Example 1, except for using 458 mg (2 mmole) of (1'R,3S)-3-[(1'-t-butyldimethylsilyloxy)ethyl]azetidin-2-one as a reaction substrate, replacing ruthenium chloride as a catalyst with each of the transition metal compounds shown in Table 2 below, using 41 mg (0.5 mmole) of anhydrous sodium acetate, 1 ml of acetic acid, 20 ml of ethyl acetate, 0.22 ml (4 mmole) of acetaldehyde, 40 ml of a 10% sodium sulfite aqueous solution, and 50 ml of a saturated sodium chloride aqueous solution, and conducting the extraction with two 100 ml portions of n-hexane.

The yield in each reaction is shown in Table 2.

TABLE 2

| Example NO. | Catalyst | Catalyst/Substrate Molar Ratio (mole %) | Percent Yield (%) |
|---|---|---|---|
| 6 | RuBr₃ | 5 | 88 |
| 7 | Ru(OAc)₃ | 5 | 83 |
| 8 | Ru₃(CO)₁₂ | 5 | 62 |
| 9 | Ru(NO)Cl₃ · H₂O | 5 | 51 |
| 10 | 1% Ru-on-graphite | 5 | 78 |
| 11 | 5% Ru-on-carbon | 5 | 56 |
| 12 | 5% Ru-on-alumina | 5 | 31 |
| 13 | OsCl₃ | 2 | 84 |
| 14 | CoCl₂ | 10 | 23 |

The titled compound was also prepared in the same manner as above by using each of Ru(TPP)(CO)—THF, RuCl₂(PPh₃)₃, and Ru-(acac) (wherein acac represents acetylacetonato) as a catalyst.

EXAMPLES 15 TO 20

Synthesis of (1'R,3R,4R)-4-Acetoxy-3-[(1'-t-butyldimethylsilyloxy)ethyl]azetidin-2-one The titled compound was prepared in the same manner as in Example 1, except for using 458 mg (2 mmole) of (1'R,3S)-3-[-(1'-t-butyldimethylsilyloxy)ethyl]azetidin-2-one as a substrate, replacing acetaldehyde with each of the aldehyde compounds shown in Table 3 below, using 41 mg (0.5 mmole) of anhydrous sodium acetate, 26 mg (0.1 mmole, 5 mole % based on the substrate) of ruthenium chloride trihydrate, 1 ml of acetic acid, 20 ml of ethyl acetate, 40 ml of a 10% sodium sulfite aqueous solution, and 50 ml of a saturated sodium chloride aqueous solution, and conducting the extraction with two 100 ml portions of n-hexane. The percent yield in each reaction is shown in Table 3.

TABLE 3

| Example No. | Aldehyde | Amount of Aldehyde (mmole) | Percent Yield (%) |
|---|---|---|---|
| 15 | propionaldehyde | 5 | 88 |
| 16 | hexanal | 5 | 90 |
| 17 | decanal | 5 | 57 |
| 18 | isobutylaldehyde | 5 | 86 |
| 19 | cyclohexanecarbaldehyde | 5 | 78 |
| 20 | crotonaldehyde | 20 | 27 |

EXAMPLE 21

Synthesis of (1'R,3R,4R)-4-Acetoxy-3-[(1'-t-butyldimethylsilyloxy)ethyl]azetidin-2-one A mixture of 458 mg (2 mmole) of (1'R,3S)-3-[(1'-t-butyl-dimethylsilyloxy)ethyl]azetidin-2-one, 41 mg (0.5 mmole) of anhydrous sodium acetate, 26 mg (0.1 mmole) of ruthenium chloride trihydrate, 1 ml of acetic acid, and 20 ml of ethyl acetate was heated to 40° C., and 6.0 g (57 mmole) of benzaldehyde was added to the solution, followed by stirring while blowing oxygen for 5 hours.

The reaction mixture was poured into 40 ml of a 10% sodium sulfite aqueous solution and extracted twice with 100 ml portions of n-hexane. The extract was washed with 50 ml of a saturated sodium chloride aqueous solution and dried over anhydrous sodium sulfate. The solvent was removed by distillation under reduced pressure, and the residue was purified by silica gel column chromatography using a 3:1 (by volume) mixed solvent of n-hexane and ethyl acetate to obtain 178 mg (0.69 mmole, percent yield: 30%) of the titled compound.

EXAMPLE 22

Synthesis of (1'R,3R,4R)-3-[(1'-t-butyldimethylsilyloxy)ethyl]-4-ethylcarbonyloxyazetidin-2-one The titled compound was synthesized in the same manner as in Example 1, except for replacing azetidin-2-one with 458 mg (2 mmole) of (1'R,3S)-3-[(1'-t-butyldimethylsilyloxy)ethyl]-azetidin-2-one, replacing acetaldehyde with 0.36 ml (5 mmole) of propionaldehyde, replacing acetic acid with 0.75 ml (10 mmole) of propionic acid, using 41 mg (0.5 mmole) of anhydrous sodium acetate, 26 mg (0.1 mmole) of ruthenium chloride trihydrate, 20 ml of ethyl acetate, 40 ml of a 10% sodium sulfite aqueous solution, and 50 ml of a saturated sodium chloride aqueous solution, and conducting the extraction with two 100 ml portions of n-hexane. The yield was 500 mg (1.95 mmole, 85%).

Melting point: 84.5° C.

$^1$H-NMR (270 MHz, CDCl$_3$) δppm: 0.06 (s, 3H), 0.08 (s, 3H), 0.87 (s, 9H, t-Bu), 1.16 (t, J=7.6, 3H), 1.26 (d, J=6.4, 3H), 2.37 (q, J=7.6, 2H), 3.18 (dd, J=3.7, 1.2, 1H), 4.22 (dq, J=6.4, 3–7, 1H), 5.84 (d, J=1.2, 1H), 6.44 (bs, 1H, NH)

EXAMPLES 23 TO 31

Each of the 4-acyloxyazetidinone compounds shown in Table 4 below was synthesized in the same manner as in Example 1, except for using 458 mg (2 mmole) of (1'R,3S)-3-[(1'-t-butyldimethylsilyloxy)ethyl]azetidin-2-one as a substrate, 10 mmole of each of the carboxylic acids shown in Table 4, 41 mg (0.5 mmole) of anhydrous sodium acetate, 26 mg (0.1 mmole) of ruthenium chloride trihydrate, 20 ml of ethyl acetate, 0.28 ml (5 mmole) of acetaldehyde, 40 ml of a 10% sodium sulfite aqueous solution, and 50 ml of a saturated sodium chloride aqueous solution, and conducting the extraction with two 100 ml portions of n-hexane. The yield and analytical results of the product are shown in Table 4. In the formulae in Table 4, Ph represents a phenyl group; t-Bu represents a t-butyl group; and Me represents a methyl group.

TABLE 4

| Example No. | Carboxylic Acid | Produced 4-Acyloxy-azetidinone Compound | Percent Yield (%) | Melting Point (°C.) | $^1$H-NMR Spectrum (270 MHz, CDCl$_3$) (δ ppm) |
|---|---|---|---|---|---|
| 23 | ClCH$_2$CO$_2$H | (1'R,3R,4R)-3-(1'-t-butyl-dimethylsilyloxy)ethyl-4-chloroacetoxyazetidin-2-one | 92 | 109 | 0.07(s, 3H), 0.08(s, 3H), 0.87(s, 9H), 1.27(d, J=6.3 3H), 3.24(dd, J=3.3, 1.2, 1H), 4.10(s, 2H), 4.24(dq, J=3.3, 6.3, 1H), 5.94(d, J=1.2, 1H), 6.44(b, 1H, NH) |
| 24 | Cl$_2$CHCO$_2$H | (1'R,3R,4R)-3-(1'-t-butyl-dimethylsilyloxy)ethyl-4-dichloroacetoxyazetidin-2-one | 70 | 118 | 0.07(s, 3H), 0.08(s, 3H), 0.87(s, 9H), 1.28(d, J=6.4, 3H), 3.32(dd, J=3.3, 1.2, 1H), 4.25(dq, J=3.3, 6.3, 1H), 5.96 (s, 1H), 6.00(d, J=1.2, 1H), 6.50(b, 1H, NH) |
| 25 | BrCH$_2$CO$_2$H | (1'R,3R,4R)-3-(1'-t-butyl dimethylsilyloxy)ethyl-4-bromoacetoxyazetidin-2-one | 78 | 107 | 0.06(s, 3H), 0.08(s, 3H), 0.87(s, 9H), 1.26(d, J=6.3, 3H), 3.24(dd, J=3.4, 1.2, 1H), 3.86(s, 2H), 4.23(dq, J=3.4, 6.3, 1H), 5.92(d, J=1.2, 1H), 6.49(b, 1H, NH) |
| 26 | Br$_2$CHCO$_2$H | (1'R,3R,4R)-3-(1'-t-butyl-dimethylsilyloxy)ethyl-4-dibromoacetoxyazetidin-2-one | 65 | 105.5 | 0.07(s, 3H), 0.09(s, 3H), 0.87(s, 9H), 1.28(d, J=6.4, 3H), 3.28(dd, J=3.4, 1.2, 1H), 4.25(dq, J=3.4, 6.4, 1H), 5.82 (s, 1H), 5.99(d, J=1.2, 1H), 6.49(b, 1H, NH) |

TABLE 4-continued

| Example No. | Carboxylic Acid | Produced 4-Acyloxy-azetidinone Compound | Percent Yield (%) | Melting Point (°C.) | $^1$H-NMR Spectrum (270 MHz, CDCl$_3$) (δ ppm) |
|---|---|---|---|---|---|
| 27 | CH$_3$OCH$_2$CO$_2$H | (1'R,3R,4R)-3-(1'-t-butyl-dimethylsilyloxy)ethyl-4-methoxyacetoxyazetidin-2-one | 74 | 80 | 0.07(s, 3H), 0.09(s, 3H), 0.87(s, 9H), 1.26(d, J=6.4, 3H), 3.22(dd, J=3.4, 1.2, 1H), 4.07(s, 2H), 4.22(dq, J=6.4, 3.4, 1H), 5.94(d, J=1.2, 1H), 6.47(b, 1H, NH) |
| 28 | PhCH$_2$CO$_2$H | (1'R,3R,4R)-3-(1'-t-butyl-dimethylsilyloxy)ethyl-4-phenylacetoxyazetidin-2-one | 83 | 61 | 0.04(s, 3H), 0.06(s, 3H), 0.85(s, 9H), 1.23(d, J=6.4, 3H), 3.18(dd, J=3.6, 1.2, 1H), 3.66(s, 2H), 4.20(dq, J=3.6, 6.4, 1H), 5.86(d, J=1.2, 1H), 6.48(b, 1H, NH), 7.24–7.36(m, 5H, aromatic) |
| 29 | 2,4-dinitro-benzoic acid | (1'R,3R,4R)-3-(1'-t-butyl-dimethylsilyloxy)ethyl-4-(2,4-dinitrobenzoyloxy)-azetidin-2-one | 54 | 148 | 0.09(s, 3H), 0.10(s, 3H), 0.90 (s, 9H), 1.30(d, J=6.3, 3H), 3.29 (dd, J=2.9, 1.2, 1H), 4.28(dq J=2.9, 6.3, 1H), 6.20(d, J=1.2, 1H), 6.53(b, 1H, NH), 7.94(d, J=8.6, 1H), 8.57(dd, J=8.6, 2.2, 1H), 8.84(d, J=2.2, 1H) |
| 30 | cyano-acetic acid | (1'R,3R,4R)-3-(1'-t-butyl-dimethylsilyloxy)ethyl-4-cyanoacetoxyazetidin-2-one | 81 | 117 | 0.06(s, 3H), 0.08(s, 3H), 0.87 (s, 9H), 1.27(d, J=6.4, 3H), 3.27 (dd, J=3.2, 1.2, 1H), 3.52(s, 2H), 4.24(dq, J=3.2, 6.4, 1H), 5.96(d, J=1.2, 1H), 6.53(b 1H, NH) |
| 31* | n-hexanoic acid | (1'R,3R,4R)-3-(1'-t-butyl-dimethylsilyloxy)ethyl-4-pentylcarbonyloxyazetidin-2-one | 61 | 60 | 0.06(s, 3H), 0.08(s, 3H), 0.88 (s, 9H), 0.90(t, J=6.8, 3H), 1.25(d, J=6.1, 3H), 1.32(m, 4H), 1.64(tt, J=7.6, 7.3, 2H), 2.34(t, J=7.3, 2H), 3.17(dd, J=3.7, 1.2, 1H), 4.22(dq, J=3.7, 6.1, 1H), 5.84(d, J=1.2, 1H), 6.49(b, 1H, NH) |

Note: *Acetaldehyde was replaced with 0.6 ml (5 mmole) of n-hexanal.

While the invention has been described in detail and with reference to specific examples thereof, it will be apparent to one skilled in the art that various changes and modifications can be made therein without departing from the spirit and scope thereof.

What is claimed is:

1. A process for preparing a 4-acyloxyazetidinone represented by formula (IV):

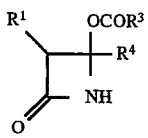

wherein $R^1$ represents a hydrogen atom, a lower alkyl group, a hydroxyethyl group, or a protected hydroxyethyl group; $R^3$ represents an alkyl group having from 1 to 10 carbon atoms which may be substituted with a halogen atom, a cyano group, a lower alkoxy group or a phenyl group, or a substituted or unsubstituted phenyl group, wherein said substituted phenyl group is substituted with a halogen atom, a lower alkoxy group or a nitro group, provided that the α-positioned carbon atom of said alkyl group should not have more than two halogen atoms; and $R^4$ represents a hydrogen atom, a lower alkyl group or a lower alkoxycarbonyl group, which comprises reacting an azetidinone represented by formula (II):

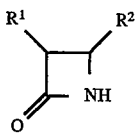

wherein $R^1$ is as defined above, and $R^2$ represents a hydrogen atom, a lower alkyl group, a lower alkoxycarbonyl group, or a carboxyl group, with a carboxylic acid represented by formula (III):

$$R^3COOH \quad (III)$$

wherein $R^3$ is as defined above, in the presence of (1) metallic ruthenium or ruthenium-on-carrier, (2) an aldehyde having 2 or more carbon atoms, which is selected from the group consisting of an alkyl aldehyde and acetaldehyde substituted with a halogen atom, a phenyl group, a lower alkoxy-substituted phenyl group or a halogen-substituted phenyl group, provided that the carbon atom at the α-position thereof should not have two or more halogen atoms, and (3) oxygen.

2. A process as claimed in claim 1, wherein said substituted phenyl group is p-chorophenyl, p-ethoxyphenyl or 2,4-dinitrophenyl.

3. A process as claimed in claim 1, wherein the reaction is carried out in the presence of a carboxylic acid salt.

4. A process as claimed in claim 1, wherein said aldehyde having 2 or more carbon atoms is selected from the group consisting of acetaldehyde, propionaldehyde, hexanal, decanal, isobutylaldehyde, cyclohexanecarbaldehyde, crotonaldehyde and benzaldehyde.

* * * * *